United States Patent
Edwards et al.

(10) Patent No.: US 10,448,729 B2
(45) Date of Patent: Oct. 22, 2019

(54) ORAL CARE DEVICE HAVING A PUMP-FREE FLUID DELIVERY SYSTEM

(71) Applicant: KONINKLIJKE PHILIPS N.V., Eindhoven (NL)

(72) Inventors: Martin John Edwards, Solihull (GB); Steven Charles Deane, Cambridge (GB); Johannes Hendrikus Maria Spruit, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 161 days.

(21) Appl. No.: 15/515,005

(22) PCT Filed: May 20, 2015

(86) PCT No.: PCT/IB2015/053704
§ 371 (c)(1),
(2) Date: Mar. 28, 2017

(87) PCT Pub. No.: WO2016/051287
PCT Pub. Date: Apr. 7, 2016

(65) Prior Publication Data
US 2017/0215569 A1    Aug. 3, 2017

Related U.S. Application Data

(60) Provisional application No. 62/056,662, filed on Sep. 29, 2014.

(51) Int. Cl.
*A46B 11/00* (2006.01)
*A61C 17/22* (2006.01)
(Continued)

(52) U.S. Cl.
CPC ........ *A46B 11/001* (2013.01); *A46B 11/0003* (2013.01); *A61C 17/0202* (2013.01);
(Continued)

(58) Field of Classification Search
CPC .................................................. A46B 11/0013
(Continued)

(56) References Cited

U.S. PATENT DOCUMENTS 8,517,728 B2  8/2013  Gatzemeyer et al.
2004/0154112 A1  8/2004  Braun et al.
(Continued)

FOREIGN PATENT DOCUMENTS

| BE | 894029 | 12/1982 |
| CN | 2358849 Y | 1/2000 |
| WO | 2012087332 A1 | 6/2012 |

*Primary Examiner* — David J Walczak
*Assistant Examiner* — Joshua R Wiljanen

(57) ABSTRACT

A powered oral care apparatus (2) has a pump-free fluid delivery system for delivering one or more fluids to the oral cavity of a user. The oral care apparatus may employ an oral care assembly (30) that has a capsule member (38) for delivering fluid through a number of openings (31, 46) in response to movement of a head (4) of the oral care apparatus. The oral care apparatus may also employ an oral care assembly (62) having a diaphragm member (84) and a mass member (88) coupled thereto wherein, in response to motion being imparted to the brushhead, the mass member and diaphragm member generate a pumping force to cause fluid to be delivered out of the oral care assembly.

14 Claims, 5 Drawing Sheets

(51) Int. Cl.
  *A61C 17/02* (2006.01)
  *A61C 17/32* (2006.01)
  *A46B 13/02* (2006.01)

(52) U.S. Cl.
  CPC ......... *A61C 17/222* (2013.01); *A46B 11/0013* (2013.01); *A46B 13/023* (2013.01); *A61C 17/32* (2013.01)

(58) Field of Classification Search
  USPC .................................................... 401/4, 291
  See application file for complete search history.

(56) References Cited

U.S. PATENT DOCUMENTS

| | | |
|---|---|---|
| 2006/0165473 A1 | 7/2006 | Hohlbein |
| 2013/0212823 A1 | 8/2013 | Bartschi et al. |
| 2013/0263397 A1 | 10/2013 | Holbein et al. |

ORAL CARE DEVICE HAVING A PUMP-FREE FLUID DELIVERY SYSTEM

CROSS-REFERENCE TO PRIOR APPLICATIONS

This application is the U.S. National Phase application under 35 U.S.C. § 371 of International Application No. PCT/IB2015/053704, filed on May 20, 2015, which claims the benefit of U.S. Provisional Patent Application No. 62/056,662, filed on Sep. 29, 2014. These applications are hereby incorporated by reference herein.

BACKGROUND OF THE INVENTION

1. Field of the Invention

The present invention pertains to a powered oral care apparatus, such as, without limitation, a power toothbrush, powered tongue cleaning device (e.g., a tongue scraper or tongue brush), or a powered tooth whitening device, and, in particular, to a powered oral care apparatus having a pump-free fluid delivery system for delivering one or more fluids to the oral cavity of a user.

2. Description of the Related Art

There are a variety of oral care devices known in the industry, including manual and powered toothbrushes, tongue cleaning devices, tooth whitening delivery systems, and chemical treatments, such as mouthwashes.

There are not, however, currently any oral care devices that efficiently and effectively combine mechanical action and fluid delivery in a single device. There is thus a need for such an oral care device.

SUMMARY OF THE INVENTION

In one embodiment, a head assembly for an oral care apparatus having a handle, a motor and a driveshaft coupled to the motor is provided. The oral care apparatus includes a coupling portion structured to enable the head assembly to be disposed on the driveshaft, an arm portion, and an oral care assembly provided at the distal end of the arm portion. The oral care assembly includes a reservoir structured to hold a fluid, and is structured to have a motion imparted thereto by the motor through the driveshaft when the head assembly is disposed on the driveshaft. The oral care assembly is also structured to dispense the fluid from the reservoir and out of the oral care assembly in response to the motion imparted by the motor.

In another embodiment, a fluid capsule member for an oral care apparatus as just described is provided. The fluid capsule member includes an upper portion, and a generally planar bottom wall portion coupled to the upper portion. The bottom wall portion has a number of first openings provided therethrough, wherein the upper portion and the planar bottom wall portion define a reservoir for holding a fluid, and wherein the fluid capsule member is structured to dispense the fluid from the reservoir and out of the distal end of the oral care apparatus through the number of first openings in response to motion imparted to arm portion the by the motor.

In still another embodiment, a head assembly for an oral care apparatus having a handle having a motor and a driveshaft coupled to the motor is provided. The head assembly includes a coupling portion structured to enable the head assembly to be disposed on the driveshaft, an arm portion coupled to the coupling portion, and an oral care assembly provided at a distal end of the arm portion. The oral care assembly is structured to oscillate about an axis in response to a motion being imparted to the arm portion through the driveshaft by the motor and includes a base member having a chamber, an inlet to the chamber and an outlet from the chamber, the inlet being structured to be fluidly coupled to a reservoir holding a fluid, a flexible diaphragm member disposed on the base member and covering the chamber, and a mass member disposed on the diagram member over the chamber on a first side of the axis. The mass member and the diaphragm member are structured to, in response to the motion being imparted to the arm portion, repeatedly move toward and away from the base member to generate a pumping force from the inlet to the outlet and cause the fluid to be delivered out of the outlet and out of the oral care assembly.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
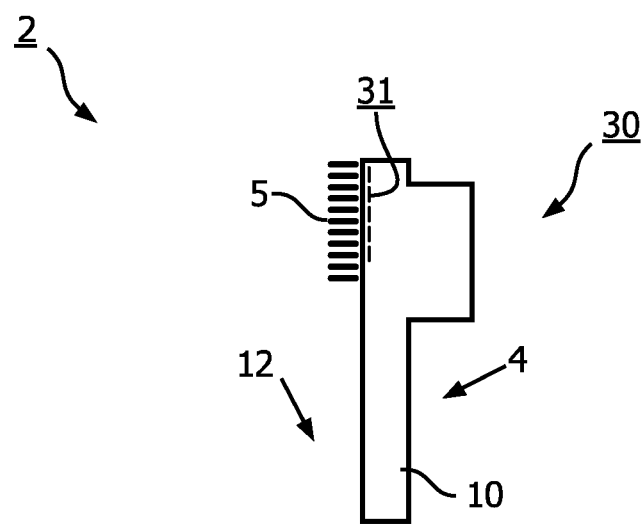
FIG. 1 is a view of a powered oral care device according to one exemplary embodiment of the present invention.
Figure 1:
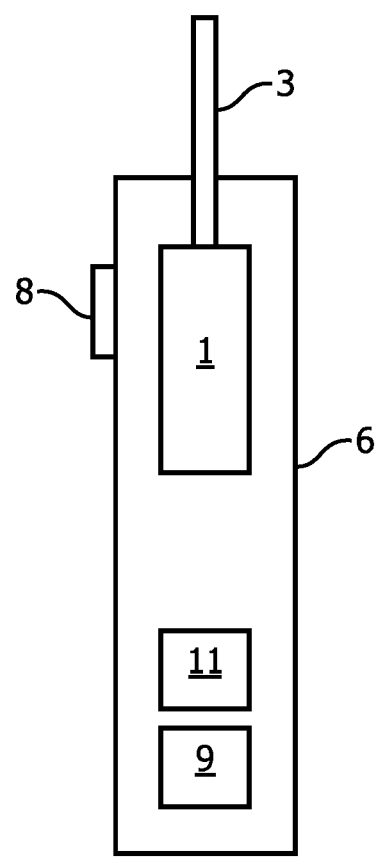

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a representational view of a powered oral care device 2 according to one exemplary embodiment of the present invention. As described in greater detail herein, oral care device 2 is, in the illustrated configuration, structured to combine chemical and mechanical oral cleaning methods in a single device by (i) including a head assembly 4 (described below) that may be selectively attached to a handle portion 6 (also described below) for removing debris, plaque, and/or biofilm from the oral cavity of the user (as assisted by the powered movement of head assembly 4 as described herein), and (ii) providing head assembly 4 with a pump-free fluid delivery system for storing and delivering a fluid, such as a tooth cleaning chemistry, mouthwash containing an antibacterial chemical, or tooth whitening chemistry, to the oral cavity of a user. In particular, rather than using motorized pumping for fluid delivery, oral care device 2 uses energy harvested from the powered mechanical motion of oral care device 2 to cause the stored fluid to be delivered to the oral cavity of a user. In addition, as described in greater detail below, in the exemplary embodiment, oral care device 2 is structured in a manner that enables different head assemblies, such as a more conventional power toothbrush assembly, to be selectively attached to the handle portion 6 as desired.

Handle portion 6 has an elongated driveshaft 3 extending from the distal end thereof and a battery powered electric motor 1 positioned within handle portion 6. Removably mounted on the driveshaft 3 is head assembly 4. The motor 1 housed within handle portion 6 is structured to move driveshaft 3, and thus head assembly 4 coupled thereto, in an oscillating manner through a selected angle. The motor 1 is powered by a rechargeable battery 9 and is controlled by controller 11 and a user-operated on/off switch 8 provided on handle portion 6. Head assembly 4 includes a coupling assembly 10 at a proximal end thereof for attaching to the drive shaft 3 of handle 6 and an arm portion 12 extending between coupling assembly 10 and oral care assembly 30 at a distal end thereof.

A number of bristles 5, form a part of and extend from oral care assembly 30 (described in detail below) at the distal end of head assembly 4, and are the primary mechanism for effectuating the mechanical cleaning function of oral care device 2. Also as seen in FIG. 1, oral care assembly 30 also includes a number of second openings 31 as described elsewhere herein.

In operation, when the motor 1 in handle portion 6 is activated and drives driveshaft 3, head assembly 4, and thus oral care assembly 30, is caused to rotate/oscillate back and forth through a selected angle. In the exemplary embodiment, oral care assembly 30 is caused to rotate/oscillate±5° at 250 Hz. As described in greater detail below, this rotation/oscillation motion simultaneously (i) assists with the mechanical operation of the bristles 5, and (ii) automatically delivers the fluid stored in oral care assembly 30 to the oral cavity of the user.

Figure 2:
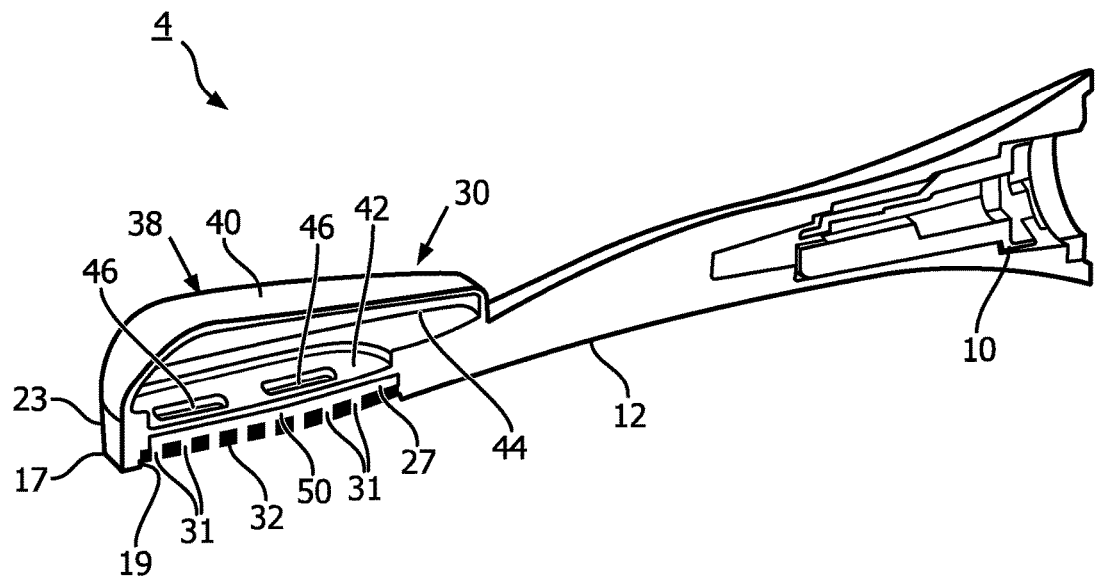
FIGS. 2 and 3 are isometric cross-sectional views of a head assembly forming a part of the powered oral care device of FIG. 1 according to the non-limiting exemplary embodiment.
Figure 3:
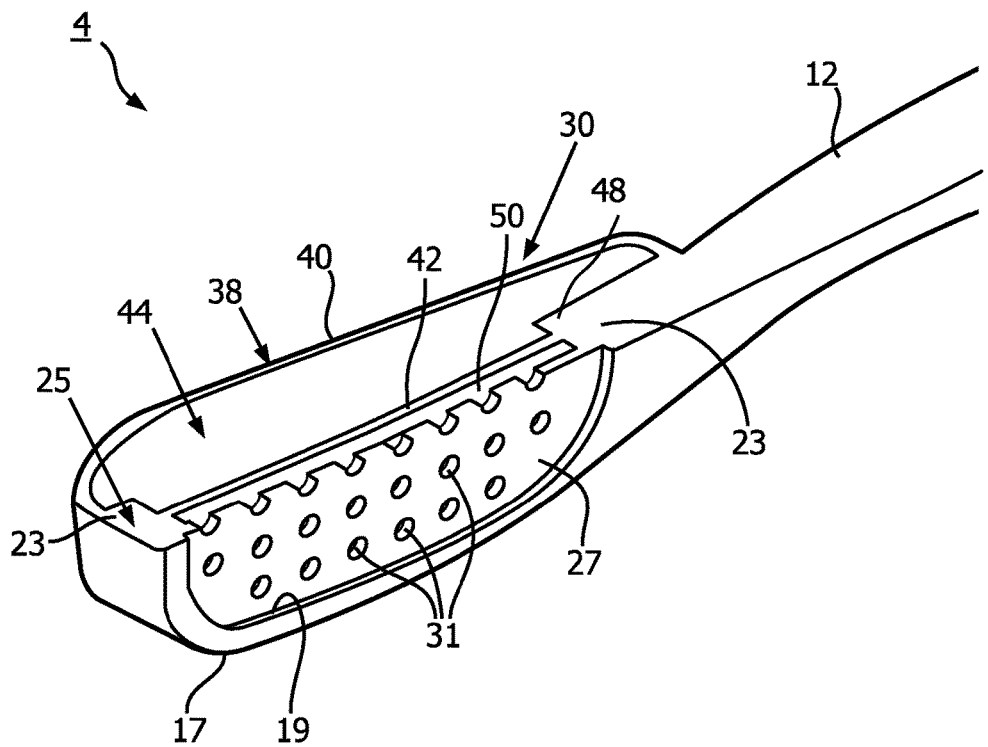

As seen in FIGS. 2 and 3, oral care assembly 30 includes an outer wall portion 19 which defines an oblong recess 23. A planar wall 27 is provided between and within outer wall 19. Planar wall 27 includes a number of second openings 31 that extend therethrough. The bristles 5 shown in FIG. 1 are attached to and extend outwardly from the outer surface of planer wall 27, with each second opening 31 being positioned adjacent to a number of the bristles 5.

It can be appreciated that the bristles 5 can be typical toothbrush bristles, or other cleaning mechanisms, such as cone shaped soft elastopolymer structures, or soft foam or sponges, although the term "bristle" as used herein is intended to more broadly encompass all of these mechanisms. Finally, oral care assembly 30 further includes a capsule member 38 that is coupled thereto, opposite planar wall 27. Capsule member 38 is structured to hold a fluid, such as a tooth cleaning chemistry, mouthwash containing an antibacterial chemical, taste enhancing chemistry, or tooth whitening chemistry, and facilitate delivery of the fluid to the oral cavity of the user through second openings 31 during use of oral care device 2.

Capsule member 38 includes an upper portion 40 coupled to a bottom generally planar wall portion 42, which together define a reservoir 44 structured to hold the fluid therein. Upper portion 40 may be made from a generally rigid material, such as polypropylene or a similar material, or may alternatively be made from a flexible material, such as silicone rubber. Bottom planar wall portion 42 has a number of first openings 46 that extend therethrough. In the exemplary embodiment, each first opening 46 has an oblong, oval-shape, although it will be understood that other shapes are also possible within the scope of the concept disclosed herein. Capsule member 38 further includes a lip member 48 which surrounds bottom planar wall portion 42. Lip member 48 is structured to be received within oral care assembly 30. In the illustrated, non-limiting exemplary embodiment, when capsule member 38 is received in the oral care assembly 30, a chamber 50 is formed between planar wall portion 27 and bottom planar wall portion 42. Chamber 50 is optional, and may be omitted in alternative embodiments. Furthermore, in still another alternative embodiment, a flow regulating member, such as a sponge, may be positioned in chamber 50 to help regulate the flow of fluid from oral care assembly 30. Alternatively, a flow regulating member, such as a sponge, may be provided as part of capsule member 38 within the space defined by lip member 48. In the exemplary embodiment, head assembly 4 is constructed such that first openings 46 will be generally aligned with second openings 31 when oral care assembly 30 is assembled. In the illustrated embodiment, second openings 31 each have a circular shape and first openings 46 each have an oblong shape. It will be understood, however, that this is meant to be exemplary only and that other shapes are also possible within the scope of the concept disclosed herein.

In the exemplary embodiment, bristles 5 are structured to exhibit hydrophobic behavior such that when capsule member 38 is coupled into oral care assembly 30, the fluid will remain within capsule member 38 even when head assembly 4 is positioned as shown in FIG. 2. This is accomplished by the material of bristles 5, and any surface coating or treatment thereon. In one embodiment, bristles 5 may be made from polydimethylsiloxane (PDMS), which is naturally hydrophobic. Also, the size of second openings 31 helps determine how difficult it is for the fluid to be released.

In operation, a user inserts the distal end of head assembly 4 including oral care assembly 30 into his or her mouth and turns on motor 1 of handle portion 6 using on/off switch 8. As elsewhere described herein, the operation of motor 1 causes head assembly 4, and in particular oral care assembly 30, to rotate/oscillate back and forth over a predetermined angle. The user may then use the oral care assembly 30, and in particular bristles 5 thereof, to clean surfaces within the oral cavity, or apply chemicals in the oral care assembly 30 to one or more surfaces within the oral cavity. For example, if oral care device 2 is a tongue cleaning device, the rotating/oscillating movement of oral care assembly 30 facilitates a scraping function to remove biofilm from the surface of the tongue and deliver chemistry that will help reduce malodor and can enhance taste sensitivity of the user. In addition, the rotating/oscillating movement of oral care assembly 30 will generate a centrifugal force that will cause the fluid stored in capsule member 38 to be delivered in a controlled manner through first openings 46 of bottom planar wall portion 42, chamber 50, and second openings 31 and past bristles 5 into the oral cavity of the user where it can be delivered to the appropriate surface therein. Thus, in this pump free arrangement, the pumping function is automatically performed by forces generated by the motion.

In various alternative embodiments, the number of openings 31, 46 and/or the dimensions of the openings 31, 46 may be adjusted to tune the pump rate of the fluid from oral care assembly 30 as desired.

Figure 4:
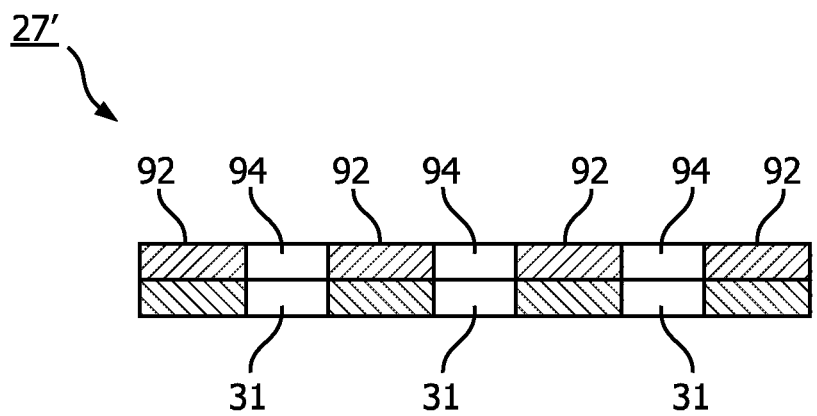
FIG. 4 is a cross-sectional view of an alternative plate member that may be used in the powered oral care device of FIG. 1.

In another example, the oral care assemblies described herein may be implemented in a device for delivering a whitening solution to the teeth of a user. In such an implementation, as shown in FIG. 4 the bristles 5 described herein may be replaced with an alternative structure, such as an applicator pad 92 having holes 94 aligned with second openings 31 in an alternative planar wall 27, that would facilitate the application of the whitening solution to the user's teeth.

Figure 5:
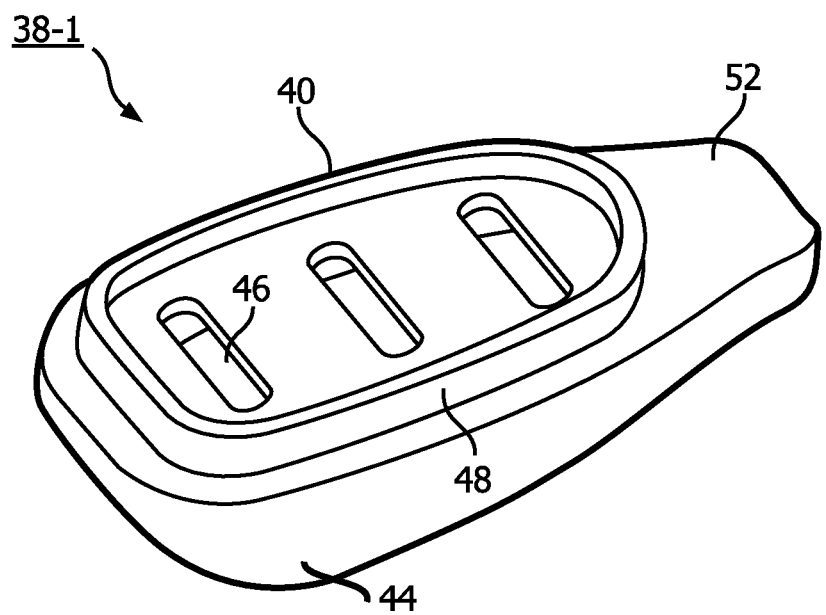
FIG. 5 is a bottom plan view of an alternative capsule member.

In one exemplary embodiment, capsule member 38 is a replaceable element as shown in FIG. 5 (labelled 38-1) that is structured to be selectively snap fit onto oral care assembly 30 and be replaced as needed. As seen in FIG. 5, this embodiment of capsule member 38 includes a sealing member 52 that is sealingly and removably attached to lip member 48 in order to contain the fluid within capsule member 38-1 until it is to be attached to oral care assembly 30. In the exemplary embodiment, sealing member 52 is made from a metallic film material that is releasably attached to lip member 48, although it will be appreciated that other configurations are also possible. When capsule member 38-1 is to be attached, sealing member 52 is removed or punctured and capsule member 38-1 is coupled to the oral care assembly 30 by inserting and snap fitting lip member 48 into recess 23 as seen in FIG. 3 so that the fluid in reservoir 44 can be delivered as described above. In such a configuration, capsule member 38-1 is friction fit to oral care assembly 30 so that oral care device 2 may be used as described above. When all of the fluid within the reservoir 44 has been dispensed, capsule 38-1 may be removed and replaced with another similarly structured capsule member 38-1.

Figure 6:
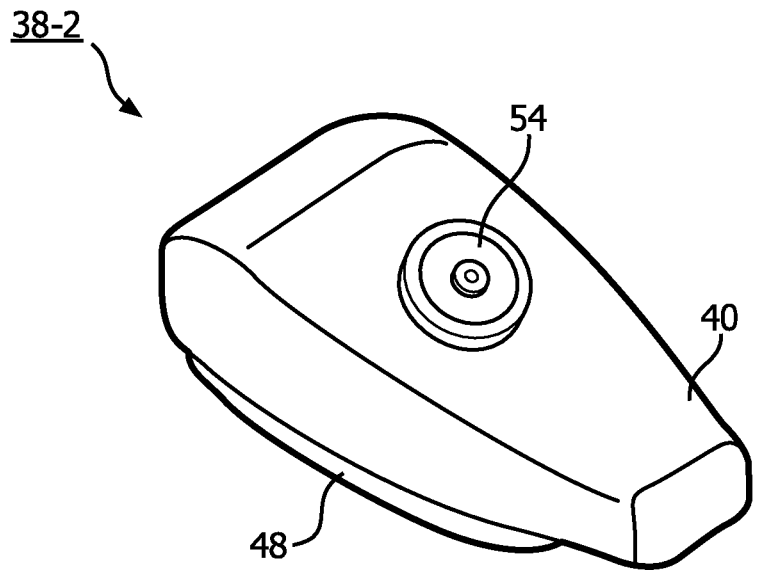
FIG. 6 is an isometric view of another alternative capsule member.

In another alternative exemplary embodiment, capsule member 38 is removably or permanently affixed to the oral care assembly 30 and is structured to be refillable with fluid as needed. For example, as shown in FIG. 6, the capsule member 38 (labeled 38-2 in FIG. 6) may have an upper portion 40 that is provided with a filling valve 54 to enable fluid to be added to the reservoir 44 in capsule member 38-2 as needed. As another example, upper portion 40 may be made from a self-sealing material that self-seals after being punctured with a needle or similar device (which would be used to fill capsule member 38) such as, without limitation, room temperature vulcanizing silicone (RTV), liquid silicone rubber (LSR), thermoplastic elastomer (TPE) or some other suitable, self-sealing elastomer material. As still another example, capsule member 38 may be refilled through the bottom of capsule member 38 using a syringe like device inserted through one of the second openings 31 and one of the first openings 46. As yet another example, upper portion 40 may be made of a flexible material, wherein refilling capsule member 38 would involve compressing upper portion 40, placing oral care assembly 30 into fluid, and then releasing upper portion 40 to draw the fluid in through openings 31 and 46.

Figure 7:
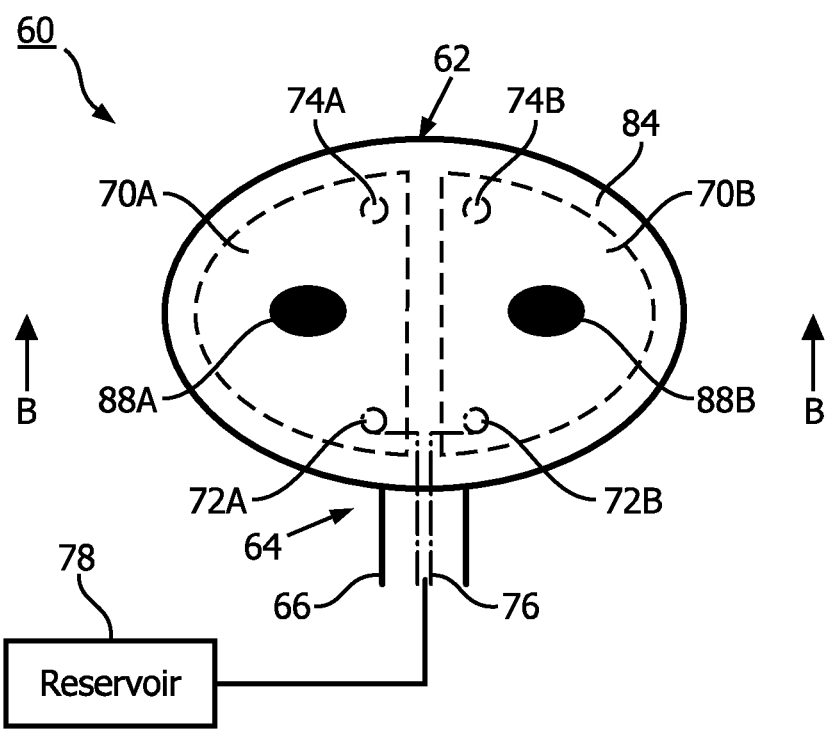
FIG. 7 is a schematic diagram of an oral care device according to an alternative exemplary embodiment.

FIG. 7 is a schematic diagram of an oral care assembly 60 according to an alternative exemplary embodiment. Oral care assembly 60, like oral care device 30, is structured to combine chemical and mechanical treatment/care methods in a single device by employing an alternative pump-free fluid delivery system for storing and delivering a fluid as described herein to the oral cavity of a user. Oral care assembly 60 is provided as part of an alternative head assembly 4' (not shown), that couples to and operates with a handle 6, such as shown in FIG. 1, as previously described.

Figure 8:
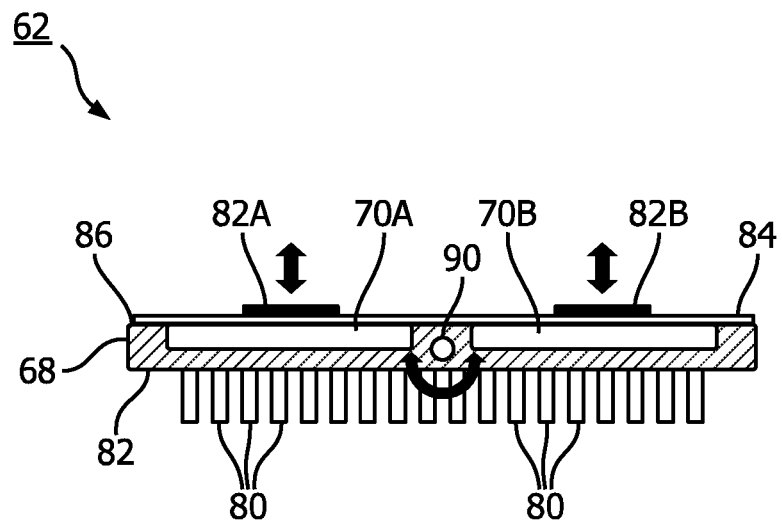
FIG. 8 is a cross-sectional view of the alternative oral care device of FIG. 7.

FIG. 8 is a cross-sectional view of oral care assembly 60 taken along lines B-B of FIG. 7. As seen in FIGS. 7 and 8, oral care assembly 60 includes a base member 68 having a first chamber 70A and a second chamber 70B. First chamber 70A has a fluid inlet 72A that provides access to first chamber 70A and a fluid outlet 74A that permits a fluid to be expelled from first chamber 70A. Similarly, second chamber 70B has a fluid inlet 72B that provides access to second chamber 70B and a fluid outlet 74B that permits a fluid to be expelled from second chamber 70B. Fluid inlets 72A and 72B are coupled to a conduit member 76 provided within arm portion 66 which is in fluid communication with a fluid reservoir 78. Fluid reservoir 78 may be mounted on a rear side of oral care assembly 60, or may also be provided within arm portion 66, or alternatively, may be provided within the handle portion 6. In the exemplary embodiment, fluid reservoir 78 holds an antibacterial fluid, such as an antibacterial mouthwash/rinse, but it can also hold tooth cleaning, taste enhancing, tooth whitening or other oral care treatment substances.

In addition, as seen in FIG. 8, oral care assembly 60 includes a number of bristles 5 that are provided on and extend from a front face 82 of base member 68. Bristles 5 are structured to be placed in the oral cavity of the user for application of the fluids contained in the oral care assembly. Fluid outlets 74A and 74B are structured such that they are open to and may dispense fluid from front face 82.

Oral care assembly 60 also includes a flexible diaphragm member 84 that is provided on a rear face 86 of base member 68. Diaphragm member 84 is structured and configured to cover and seal the tops of the first and second chambers 70A, 70B. Diaphragm member 84 is made of a suitable flexible material such as, without limitation, liquid silicone rubber.

Oral care assembly 60 further includes a first mass member 88A provided on the top surface of diaphragm member 84 in a position over first chamber 70A and a second mass member 88B provided on the top surface of diaphragm member 84 in a position over second chamber 70B. In one embodiment, first and second mass members 88A, 88B are separate components, such as plastic or metal discs, that are coupled to the top surface of diaphragm member 84 by a suitable method such as using an adhesive. In an alternative embodiment, first and second mass members 88A, 88B are thickened portions of diaphragm member 84 that are formed integrally therewith at the locations shown in FIGS. 7 and 8.

In operation, when oral care assembly 60 is caused to rotate/oscillate back and forth about axis 90 by the motor of handle portion 6, mass members 88A and 88B move alternatively in the direction shown by the arrows in FIG. 8 so as to cause the portion of diaphragm member 84 to which they are attached to alternately move upwards and downwards. This alternating movement changes the volume of first chamber 70A and second chamber 70B in a cyclic manner. Moreover, as seen in FIG. 8, first chamber 70A and second chamber 70B are provided on opposite sides of axis of rotation 90 of oral care assembly 60. This means that when one of the chambers increases in volume, the other chamber decreases in volume. Thus, as oral care assembly 60 rotates over its limited range of angles, mass members 88A and 88B cause the volumes of the associated chambers 70A, 70B, to increase and decrease in an alternating fashion. When the volume of a chamber increases, fluid is drawn from reservoir 78 to fill that chamber. When the volume of a chamber decreases, fluid is forced out through fluid outlets 74A, 74B of that chamber and is delivered from oral care assembly 60 past bristles 5.

Fluid inlets 72A and 72B may incorporate a valve member which allows fluid to enter the associated chamber 70A, 70B, but which prevents fluid from returning to reservoir 78. Similarly, fluid outlets 74A, 74B may incorporate a valve member which allows fluid to leave the associated chamber 70A, 70B, but which prevents fluid from entering the associated chamber 70A, 70B through the outlet.

Thus, oral care assembly 60 provides an alternative mechanism wherein rotational/oscillatory motion simultaneously (i) assists with the delivery of fluid to the oral cavity of the user.

Figure 9:
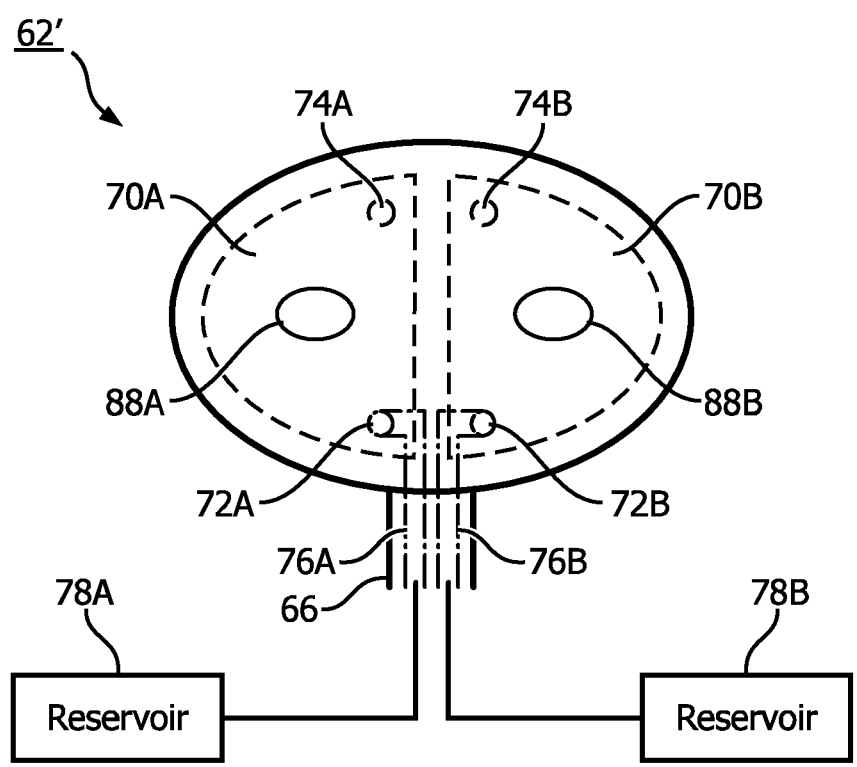
FIG. 9 is a schematic diagram of an oral care device according to another alternative exemplary embodiment.

In still another example, an alternative oral care assembly 60' as shown in FIG. 9 (similar to oral care assembly 60) may be used to mix and deliver a two-part fluid solution to the oral cavity of a user. More specifically, in such an implementation, oral care assembly 60' is coupled to two separate reservoirs 78A, 78B, with each reservoir holding one of the fluids of the two-part solution. As will be appreciated, those two fluids will be kept separate and will be mixed immediately before being dispensed from oral care assembly 60' as described herein. This would be particularly advantageous for two-part solutions that can harden or degrade after being mixed.

Furthermore, it will be understood that that the disclosed concept may be employed in connection with an oral care device configured to provide different oral care functionality. For example, the oral care assemblies described herein may be provided with bristles that are conventional toothbrush bristles such that the disclosed concept can be implemented in a powered toothbrush device which is able to simultaneously clean teeth and deliver an anti-bacterial fluid to the oral cavity of the user that can be used to reduce malodor and can enhance taste sensitivity.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A powered oral care apparatus comprising:
   a handle having a motor and a driveshaft coupled to the motor;
   a head assembly having an arm portion, a coupling portion structured to enable the head assembly to be disposed on the driveshaft, and an oral care assembly provided at a distal end of the arm portion, wherein the oral care assembly includes a fluid capsule member provided on a first side of the distal end of the arm portion, the capsule member including an upper portion and a bottom generally planar wall portion defining a reservoir structured to hold a fluid, the bottom wall portion having a number of first openings provided therethrough, wherein the oral care assembly is structured to have a motion imparted thereto by the motor through the driveshaft when the head assembly is disposed on the driveshaft, and wherein the oral care assembly is structured to dispense the fluid from the reservoir and out of the number of first openings in the oral care assembly in response to the motion imparted by the motor.

2. The oral care assembly according to claim 1, wherein the fluid capsule member further includes a lip member coupled to the bottom planar wall portion, the lip member being structured to be received within a recess provided in the oral care assembly.

3. The oral care assembly according to claim 2, wherein the fluid capsule member is structured to be removably coupled to the oral care assembly.

4. The powered oral care apparatus according to claim 1, wherein the oral care assembly further comprises an outer wall portion defining a planar wall portion the planar outer wall portion of the oral care assembly having a number of second openings provided therethrough, and wherein the oral care assembly is structured to dispense the fluid from the reservoir and out of the oral care assembly through the number of first openings of the reservoir and the number of second openings of the oral care assembly in response to the motion imparted by the motor.

5. The powered oral care apparatus according to claim 4, wherein the outer wall portion of the oral care assembly includes a number of bristles attached to and extending outwardly from an outer surface thereof.

6. The powered oral care apparatus according to claim 1, wherein the upper portion of the capsule member includes a valve member for refilling the reservoir.

7. An oral care assembly for an oral care apparatus having a handle having a motor and a driveshaft coupled to the motor, and a head assembly coupled to the handle; wherein the oral care assembly is structured to be coupled to a distal end of the head assembly;

the oral care assembly comprising an outer wall portion defining a planar wall portion the planar wall portion having a number of second openings provided therethrough, and a fluid capsule member comprising an upper portion; and a bottom generally planar wall portion coupled to the upper portion, the bottom wall portion having a number of first openings provided therethrough, wherein the upper portion and the bottom wall portion define a reservoir for holding a fluid, and wherein the fluid capsule member is structured to dispense the fluid from the reservoir through the number of first openings and the number of second openings in response to motion imparted to arm portion the by the motor.

8. The fluid capsule member according to claim 7, further comprising a lip member coupled to the bottom planar wall portion the lip member being structured to be received within a recess provided in the oral care assembly.

9. The fluid capsule member according to claim 7, wherein the upper portion of the capsule member includes a valve member for refilling the reservoir.

10. An oral care assembly for a powered oral care device having a handle having a motor and a driveshaft coupled to the motor, comprising:

a head assembly having an arm portion, a coupling portion structured to enable the head assembly to be disposed on the driveshaft, the oral care assembly located at a distal end of the arm portion;

wherein the oral care assembly is structured to oscillate about an axis in response to a motion being imparted to the arm portion through the driveshaft by the motor and includes:

a base member having a chamber, an inlet to the chamber and an outlet from the chamber, the inlet being structured to be fluidly coupled to a reservoir holding a fluid, a flexible diaphragm member disposed on the base member and covering the chamber, and a mass member) disposed on the diagram member over the chamber on a first side of the axis;

wherein the mass member and the diaphragm member are structured to, in response to the motion being imparted to the arm portion, repeatedly move toward and away from the base member to generate a pumping force from the inlet to the outlet and cause the fluid to be delivered out of the outlet and out of the oral care assembly.

11. The head oral care assembly according to claim 10, wherein the diaphragm member is provided on a first surface of the base member, wherein the outlet is structured to dispense the fluid from a second surface of the base member opposite the first surface, and wherein the head assembly includes a number of bristles extending from the second surface.

12. The oral care assembly according to claim 10, wherein the base member has a second chamber, a second inlet to the second chamber and a second outlet from the second chamber, the second inlet being structured to be fluidly coupled to the reservoir, wherein the diaphragm member covers the second chamber, wherein the head assembly includes a second mass member (disposed on the diagram member over the second chamber on a second side of the axis opposite the first side of the axis, and wherein the second mass member and the diaphragm are structured to, in response to the motion being imparted to the arm portion, repeatedly move toward and away from the base member to generate a pumping force from the second inlet to the second outlet and cause the fluid to be delivered out of the outlet and out of the oral care assembly.

13. The oral care assembly according to claim 12, wherein the diaphragm member is a first diaphragm covering the first chamber and a second diaphragm covering the second chamber.

14. The oral care assembly according to claim 10, wherein the base member has a second chamber, a second inlet to the second chamber and a second outlet from the second chamber, the second inlet being structured to be fluidly coupled to a second reservoir holding a second fluid, wherein the diaphragm member covers the second chamber, wherein the head assembly includes a second mass member disposed on the diagram member over the second chamber on a second side of the axis opposite the first side of the axis, and wherein the second mass member and the diaphragm are structured to, in response to the motion being imparted to the arm portion, repeatedly move toward and away from the base member to generate a pumping force from the second inlet to the second outlet and cause the second fluid to be delivered out of the outlet and out of the oral care assembly.

* * * * *